United States Patent [19]

Yoh

[11] Patent Number: 4,904,524

[45] Date of Patent: Feb. 27, 1990

[54] WET WIPES

[75] Inventor: Ho-ward J. Yoh, W. Berlin, N.J.

[73] Assignee: Scott Paper Company, Philadelphia, Pa.

[21] Appl. No.: 259,076

[22] Filed: Oct. 18, 1988

[51] Int. Cl.$^4$ .................. A47K 7/03; A61M 35/00; D21D 3/00; D21H 3/32

[52] U.S. Cl. .................. 428/311.3; 162/135; 162/164.1; 162/179; 424/401; 424/402; 424/414; 427/180; 428/308.8; 428/311.7; 428/321.5

[58] Field of Search ............ 424/401, 402, 414; 428/308.8, 311.3, 311.7, 321.5; 427/180; 162/135, 164.1, 179

[56] References Cited

U.S. PATENT DOCUMENTS

| | | | |
|---|---|---|---|
| 4,401,712 | 8/1983 | Morrison | 428/907 |
| 4,426,418 | 1/1984 | Coleman et al. | 424/414 |
| 4,550,035 | 10/1985 | Smith | 424/401 |
| 4,559,157 | 12/1985 | Smith et al. | 428/320.2 |
| 4,615,937 | 10/1986 | Bouchette | 428/289 |
| 4,655,756 | 4/1987 | Fawkes | 424/402 |
| 4,690,821 | 9/1987 | Smith et al. | 424/401 |
| 4,690,825 | 9/1987 | Won | 424/501 |
| 4,772,501 | 9/1988 | Johnson et al. | 428/289 |
| 4,786,367 | 11/1988 | Bogart | 424/401 |

FOREIGN PATENT DOCUMENTS 1168157  5/1984  Canada .

Primary Examiner—James C. Cannon
Attorney, Agent, or Firm—John A. Weygandt; John W. Kane, Jr.

[57] ABSTRACT

A wet wipe comprising a porous sheet impregnated with an aqueous lotion and, concentrated near the surface of the sheet, polymeric beads containing a functional ingredient which is useful for treating the human skin or environmental surfaces and which are characterized in providing controlled release of the functional ingredient, and methods of making said wet wipe.

11 Claims, No Drawings

WET WIPES

BACKGROUND OF THE INVENTION

1. Field of the Invention

The present invention relates to a wet wipe comprising a porous sheet impregnated with an aqueous lotion and further including polymeric beads which are characterized in providing controlled release of a functional ingredient.

2. Description of Related Art

A variety of treated cloths which are adapted for skin care are commercially available. Such products typically comprise paper or non-woven fabric sheets which are wetted with a aqueous solution of water soluble or water dispersible ingredients. The difficulty presented by these ingredients is that they are typically water insoluble or hydrophobic. It is well-known to incorporate hydrophobic cosmetic ingredients in the form of an oil-in-water emulsion. See U.S. Pat. No. 4,559,157, granted Dec. 17, 1985 to Smith et al, "Cosmetic Applicator Useful for Skin Moisturizing". The drawback of the oil-in-water emulsion approach is twofold. One is that these emulsions tend to be unstable; secondly, the chemicals which emulsify the hydrophobic materials also tend to keep such components from uniformly adhering to the human skin.

Accordingly, it is an object of the present invention to provide hydrophobic functional ingredients in a wet wipe in a stable form.

It is a further object of the present invention to controllably release such functional ingredients when applied to the human skin or environmental surfaces.

Other objects advantages and novel features of the present invention will be apparent to those skilled in the art from the following description and appended claims.

SUMMARY OF THE INVENTION

The objects of the present invention are attained by providing a wet wipe comprising a porous sheet which is impregnated with an aqueous lotion and, concentrated near the surface of the sheet, polymeric beads containing a functional ingredient which is useful for treating the human skin or environmental surfaces and which are characterized in providing controlled release of the functional ingredient.

As used herein, the term "polymeric beads" shall mean any form of discrete, free-flowing powders or beads which envelope, coat or contain an active ingredient in a polymeric matrix or capsule. Such beads provide for the controllable release over time of the active ingredient either by rupture of the coating or matrix whereby the active ingredient is released when sufficient pressure or shearing action is applied to the bead or the coating or matrix may be semipermeable or porous to allow the active ingredient to diffuse out of the bead. Additionally, as will be appreciated by skill in the pertinent art, the application of heat may lower the viscosity of the entrapped material (or raise its vapor pressure) thereby causing more rapid release from the porous polymeric beads. "Polymeric beads" is intended to encompass microcapsules generally; microcapsules being a well-known form of polymeric beads formed by emulsion polymerization. The term further includes beads formed by polymer entrapment as described in Canadian Pat. No. 1,168,157 and porous beads claimed in U.S. Pat. No. 4,690,825.

Entrapment in a polymer matrix is disclosed in Canadian Pat. No. 1,168,157, issued May 29, 1984 to Eric S. Abrutyn, entitled "Polymer Entrapped Emollient-Moisturizer Composition". According to Abrutyn, water insoluble organic liquids and solids can be entrapped in a hydrophobic polymeric lattice. The polymeric lattice functions to hold and protect the entrapped material and is capable of providing availability of the entrapped material by a variety of mechanisms, particularly pressure. Such materials are commercially available from Wickhen Products, Inc. under the trademark POLYTRAP.

The term porous beads or "microsponges" refers to the time-release delivery vehicles disclosed and claimed in U.S. Pat. No. 4,690,825, granted Sept. 1, 1987 to Richard Won, "Method for Delivering an Active Ingredient by Controlled Time Release Utilizing a Novel Delivery Vehicle which can be Prepared by a Process Utilizing the Active Ingredient as a Porogen".

All of these types of polymeric beads are characterized in providing release of an active ingredient from a network of pores, while the shape of the entrapping cavity and the external shape of the particular may vary. The POLYTRAP polymeric lattices and microsponges have in common the feature that the active or functional ingredient is trapped in a network of pores or cavities during polymerization. The active ingredient thereby has a substantially uniform concentration throughout the network of pores. This uniformity helps to create a more controlled release of the active ingredient from the network of pores over a given period of time (controlled time-release). As these structures provide a sustained release over a period of time as compared to a total release when the membrane of a microcapsule is broken, they are preferred for use in the present invention. Microcapsules are nonetheless capable of providing time release in many applications where not all of the microcapsules are ruptured at once.

The present inventor contemplates that a wide variety of water insoluble organic liquids and solids may be incorporated within the polymeric beads. The term "functional ingredient" can be defined as any ingredient which when released from the polymeric beads performs some function relative to the surface to which it is applied. Thus, if the wet wipes of the present invention are to be applied to the human skin, the active ingredient may be a drug or beauty aid and might comprise anti-infectives such as antibiotics, antimicrobials and fungicides, antiperspirants, deodorants, sunscreens, emollients, humectants and insect repellants. If they are to be used for wiping environmental surfaces in the home or for agricultural, food service, veterinary or medical applications, the functional ingredient might be a wax or polish, a fragrance, a disinfectant or an insecticide.

The term "aqueous lotion", as used in this specification and the appended claims, refers to any aqueous solution, including hydrogels, and oil-in-water emulsions.

As will be appreciated by one of ordinary skill in the art to which the present invention pertains, the polymeric beads of the present invention are applied at concentrations which provide the transfer of an effective amount of the functional ingredient to the skin or surface when the pre-moistened sheet is pressed or rubbed against the skin or surface.

Cellulosic fibrous webs are preferred as the porous sheet for the wet wipe of the present invention because of their low cost and biodegradability. Especially preferred are paper, air-laid and carded non-woven webs. However, spun-bonded and spun-lace webs are also suitable. For applications where cost and/or biodegradability are not important, alveolar polymeric films, foam and other porous sheets may be employed. Techniques for moistening the wipes and packaging them in moisture impervious packages are well-known in the art and need not be elaborated here.

The feature which the present inventor believes is fundamental to the success of her invention is the concentration of the polymeric beads at or near the surface of the porous sheet. In this way the maximum amount of the functional ingredient which was applied to the sheet will be transferred to the surface to be treated. The present inventor has found that the polymeric beads, because of their particular nature, when applied to the surface of the sheet, tend to remain near the surface of the sheet and not to penetrate the sheet like a liquid does. Most preferably, the polymeric beads are applied to the sheet before or after the sheet has been impregnated with water or an aqueous lotion. The beads in dry form can be dusted, sifted or sprayed onto the sheet. Alternatively, they can be printed or roll coated in the form of a printing fluid or paste. Less preferably, the polymeric beads can be combined with the aqueous lotion and applied to the web which has already been wetted with water so that the polymeric beads are not carried into the interior of the web as readily when the lotion strikes through a dry web. It is also feasible to apply the polymeric beads with the aqueous lotion to a dry web. However, in the latter case, the beads will not be as concentrated near the surface as when applied to a previously wetted web. The present inventor has found that a more convenient and efficient manufacturing process results when the step of combining the polymeric beads with the aqueous lotion is avoided; i.e., it is generally easier to apply the polymeric beads separately in dry form than to disperse them uniformly in the lotion. As will be understood by one skilled in the pertinent art, the selection of the method of application will be determined largely by the intended use of the wet wipe, as will be illustrated by the following description of the preferred embodiments.

DETAILED DESCRIPTION OF THE INVENTION

The invention will be further described with reference to the following detailed examples, which illustrate the preparation of wet wipes for treating the human skin and environmental surfaces utilizing the teachings of the present invention.

Emollient oils generally function to lubricate the skin surface and to prevent evaporative loss of skin moisture supplied by underlying tissues. They also function to provide a protective barrier against environmental irritants. The emollient oils useful in the practice of the present invention include those commonly employed in the art such as liquid hydrocarbons, e.g., petrolatum, mineral oil and the like, vegetable and animal fats and oils, viz. lanolin, phospholipids and their derivatives and silicones. Silicones, especially dimethicones are preferred for providing a protective barrier and may consist of one or more of the commercially available dimethicones or linear polydimethylsiloxane polymers having a viscosity in the range of 50 to 1,00 centistokes. Preferably, the dimethicones will be present at about 0.5% to 30% by weight of the web or porous sheet.

EXAMPLE I

Non-Greasy Barrier Wipe

A lotion formulated as shown below was used as a base lotion to lotionize an air-laid, non-woven web having a basis weight of 68 grams per square meter to 300% of the web weight (i.e. about 200 grams lotion per square meter web.) The lotion was applied by immersing the web in the lotion followed by roll doctoring the web to the desired degree of saturation.

| Ingredient | % by Weight of Lotion |
| --- | --- |
| Bronopol | .05 |
| Methylparaben | .2 |
| Propylparaben | .03 |
| Propylene Glycol | 1.5 |
| Water to make up 100% | Microsponges | containing 50% dimethicone by weight were applied to each side of the non-woven web by fluidizing them in air and spraying them onto the web. The microsponges were applied to each side at the rate of 5% of the dry web weight to make a product containing 10% by weight microsponges or 5% by weight dimethicone. When used to wipe the skin, the wipe deposited the microsponges and expressed dimethicone onto the skin during the wiping action. The dimethicone layer on the skin provided a barrier to protect the skin. The microsponges transferred to the skin continued to provide time-release of dimethicone. Such a wipe may be used as a baby wipe to help prevent diaper rash.

EXAMPLE II

Low SPF Sun Screen Wipe

A spun lace web having a basis weight of 85 grams per square meter is lotionized using the formulation of Example I in the same manner and at the same rate. Microsponges containing a mixture of oxybenzone and octyl dimethyl p-amino benzoate in the ratio of one to three respectively were applied to each side of the wetted non-woven web by the same method as in Example I. The microsponges are applied to each side at the rate of 7% of the weight of the dry web to make a product containing 14% by weight of microsponges or 7% by weight of functional ingredients. The product is non-greasy and when rubbed onto the skin to be protected from sunburn provided protection against the burning rays of the sun; namely, UVA (light of 320 to 400 nanometers in wave length) and UVB (light of 290–320 nanometers in wave length) at a SPF (Sun Protection Factor) level of 4 as measured by the procedure specified by the Food and Drug Administration in the Over-the-Counter Monograph on Sunscreen Drug Products for Over-the-Counter Human Drugs, Proposed Safety, Effective and Labelling Conditions. Fed. Register. 43(166); 38206–38269, Aug. 25, 1978.

EXAMPLE III

High SPF Sun Screen Wipe

In the present example, sun blocking agents are also included in the formulation used to lotionize the web, namely:

| Ingredient | % Weight of Lotion |
| --- | --- |
| Oxybenzone | 3 |

| Ingredient | % Weight of Lotion |
| --- | --- |
| Ethylhexyl p-methoxy cinnamate | 6 |
| PPG-3 myristyl ether (surfactant) | 5 |
| Isopropyl Myristate | 4 |
| Glyceryl Stearate | 2 |
| Myristyl Alcohol | 2 |
| PEG-20 methyl glucose sesquistearate (emulsifier) | 2 |
| preservative | 0.1 |
| perfume | 0.3 |
| Water | 75.4 |

Microsponges are then applied as in Example II. The resulting product is moisturizing to the skin and provides sunburn protection at an SPF level of 20.

EXAMPLE IV

Non-Greasy Moisturizing Wipe for Hand and Body

An oil-in-water emulsion of the following formulation:

| Ingredient | % by Weight of Lotion |
| --- | --- |
| Mineral oil | 2 |
| Propylene glycol | 1.5 |
| methylparaben | 0.30 |
| propylparaben | 0.04 |
| ethoxylated sorbitol fatty acid ester (surfactant) | 0.4 |
| water to make up 100% | | in which is dispersed POLYTRAP polymeric lattices containing 80% by weight dimethicone in an amount equal to 2% by weight of the emulsion is applied at the rate of 300% by weight of the dry web to a carded web made of a 50/50 blend of polyester and rayon and having a basis weight of 51 grams per square meter by means of a constant flow applicator to the web which is moving at a controlled velocity. This wipe feels non-greasy and provides good moisturizing effect for the skin.

EXAMPLE V

Insect Repellent Wipe

The carded web of Example IV was lotionized with a 2% mineral oil emulsion as described in Example IV which included in place of the polymeric beads containing dimethicone microsponges loaded with the insect repellent DEET-diethyl toluamide at 50% by weight were uniformly dispersed in the lotion at 5% by lotion weight. This wipe provided the insect repelling function but with a more pleasant feel because of the controlled release of the DEET from the polymeric beads and the lubricating effect of the mineral oil. Moreover, the mineral oil would have been difficult to include had the DEET not been entrapped in the polymeric beads.

EXAMPLE VI

Barrier Wipe for Dry Skin

A non-woven web made of 100% wood pulp having a basis weight of 68 grams per square meter is lotionized by the method described in Example IV to 280% of the dry web weight with an emulsion lotion containing 3% dimethicone as shown below.

| | |
| --- | --- |
| dimethicone | 3 |
| ethoxylated sorbitol fatty acid ester (surfactant) | 0.5 |
| methylparaben | 0.2 |
| propylparaben | 0.03 |
| bronopol | 0.05 |
| water to make up 100% | |

A paste consisting of 70% by weight microsponges containing 50% by weight mineral oil and of 30% of distilled water is then printed onto the lotionized web by using a gravure roll. Using this technique, said microsponges were applied to each side at the rate of 7% by dry weight of the web to make a product containing 14% by weight microsponges or 7% of mineral oil. This wipe product is moisturizing and provides an enduring barrier effect to dry skin.

EXAMPLE VII

Lubricating Shaving Wipe for Legs

A non-woven carded web as described in Example IV is lotionized with an aqueous lotion as described in Example I to 250% of the dry web weight. Microcapsules containing dimethicone are then applied to the lotionized web as in Example I. This product can be used for lubricating skin prior to shaving the legs.

EXAMPLE VIII

Cleansing and Waxing Wipe for Furnitures

An airlay web as described in Example I is lotionized with a base lotion as described below to 285% of the dry web weight.

| | |
| --- | --- |
| ethoxylated sorbitol fatty acid ester (surfactant) | 0.5 |
| methylparaben | 0.2 |
| propylparaben | 0.03 |
| propylene glycol | 1.5 |
| bronopol | 0.05 |
| water to make up 100% | |

Microsponges containing furniture wax are then applied to the lotionized web by the method described in Example I to the extent of 30% of the dry weight. This product is used to clean and wax furniture in one step.

While certain representative embodiments of the invention have been described herein for purposes of illustration, it will be apparent to those in the skilled in the art that modifications thereof may be made without parting from the spirit and scope of the invention as defined by the appended claims.

I claim:

1. A porous sheet impregnated with an aqueous lotion comprising a hydrophobic functional ingredient entrapped in polymeric beads, said entrapped ingredient being concentrated near the surface of the sheet.

2. The sheet according to claim 1 wherein the beads are microsponges.

3. The sheet according to claim 1 wherein the beads are microsponges in the form of a polymeric matrix.

4. The sheet according to claim 1 wherein the beads are microcapsules.

5. The sheet according to claim 1 wherein said functional ingredient is dimethicone present in an amount between 0.5% to 30% by weight of the porous sheet.

6. The method of making a wet wipe comprising a porous sheet impregnated with an aqueous lotion wherein the improvement comprises applying polymeric beads containing a hydrophobic functional ingredient.

7. The method of claim 6 wherein said beads are applied in dry form.

8. The method of claim 6 wherein said beads are applied in the form of a paste.

9. The method of claims 6, 7 or 8 wherein said beads are applied before the sheet is impregnated with the aqueous lotion.

10. The method of claims 6, 7 or 8 wherein said beads are applied after the sheet is impregnated with the aqueous lotion.

11. The method of claim 6 wherein said beads are mixed with the aqueous lotion when applied to the sheet.

* * * * *